United States Patent [19]

Orndorff

[11] Patent Number: 4,478,683
[45] Date of Patent: * Oct. 23, 1984

[54] ENZYMATIC CATALYZED BIOCIDE SYSTEM

[75] Inventor: Steve A. Orndorff, Columbia, Md.

[73] Assignee: Westvaco Corporation, New York, N.Y.

[*] Notice: The portion of the term of this patent subsequent to Jan. 25, 2000 has been disclaimed.

[21] Appl. No.: 424,374

[22] Filed: Sep. 27, 1982

Related U.S. Application Data

[63] Continuation of Ser. No. 319,298, Nov. 9, 1981, Pat. No. 4,370,199.

[51] Int. Cl.$^3$ .............................................. D21F 1/66
[52] U.S. Cl. ...................................... 162/161; 162/190; 210/606; 210/632; 210/764; 210/928; 435/190; 435/192; 435/800
[58] Field of Search ................ 162/161, 190; 210/609, 210/632, 764, 928; 435/190, 192, 800, 25, 28, 810; 422/29, 37

[56] References Cited

U.S. PATENT DOCUMENTS

| | | | |
|---|---|---|---|
| 1,844,018 | 2/1932 | Sailer | 435/192 |
| 3,817,835 | 6/1974 | Neidleman | 435/192 |
| 3,824,184 | 7/1974 | Hatcher et al. | 210/632 |
| 3,994,772 | 11/1976 | Sweved et al. | 162/161 |
| 4,199,600 | 4/1980 | Brandman et al. | 404/314 |

OTHER PUBLICATIONS

Bergmeyer, H. V. "Methods of Enzymatic Analysis", vol. 2, Academic Press Inc., New York, NY, 1976, pp. 685–689.
Barman, T. E., "Enzyme Handbook", vol. 1, Springer-Verlag Inc., New York, NY, 1969, p. 228.
Applied & Environmental Microbiology Nov. 1979, pp. 821–826, vol. 38, No. 5.
Phytopathology, vol. 65, No. 6, Jun. 1975, pp. 686–690, Urs et al.
Chemical & Engineering News, Sep. 14, 1981, p. 53, "Horseradish Peroxidase Cleans Up Wastewater".
Journal of Bacteriology, vol. 99, No. 2, Aug. 1969, pp. 361–365.
Science, Jan. 9, 1970, pp. 195–196, "Peroxidase-Mediated Virucidal Systems".
Infection & Immunity, Jul. 1979, pp. 110–116., vol. 25, 1979.

*Primary Examiner*—William Smith

[57] ABSTRACT

A method of killing and inhibiting the growth of microorganisms in industrial process streams comprises the addition of an enzymatically catalyzed biocide system utilizing a microbial or plant dehydrogenase enzyme such as peroxidase or laccase in the presence of an oxidant such as hydrogen peroxide or oxygen to oxidize phenolic compounds found in or added to the process streams to produce oxidation products that are toxic to microorganisms.

6 Claims, 1 Drawing Figure

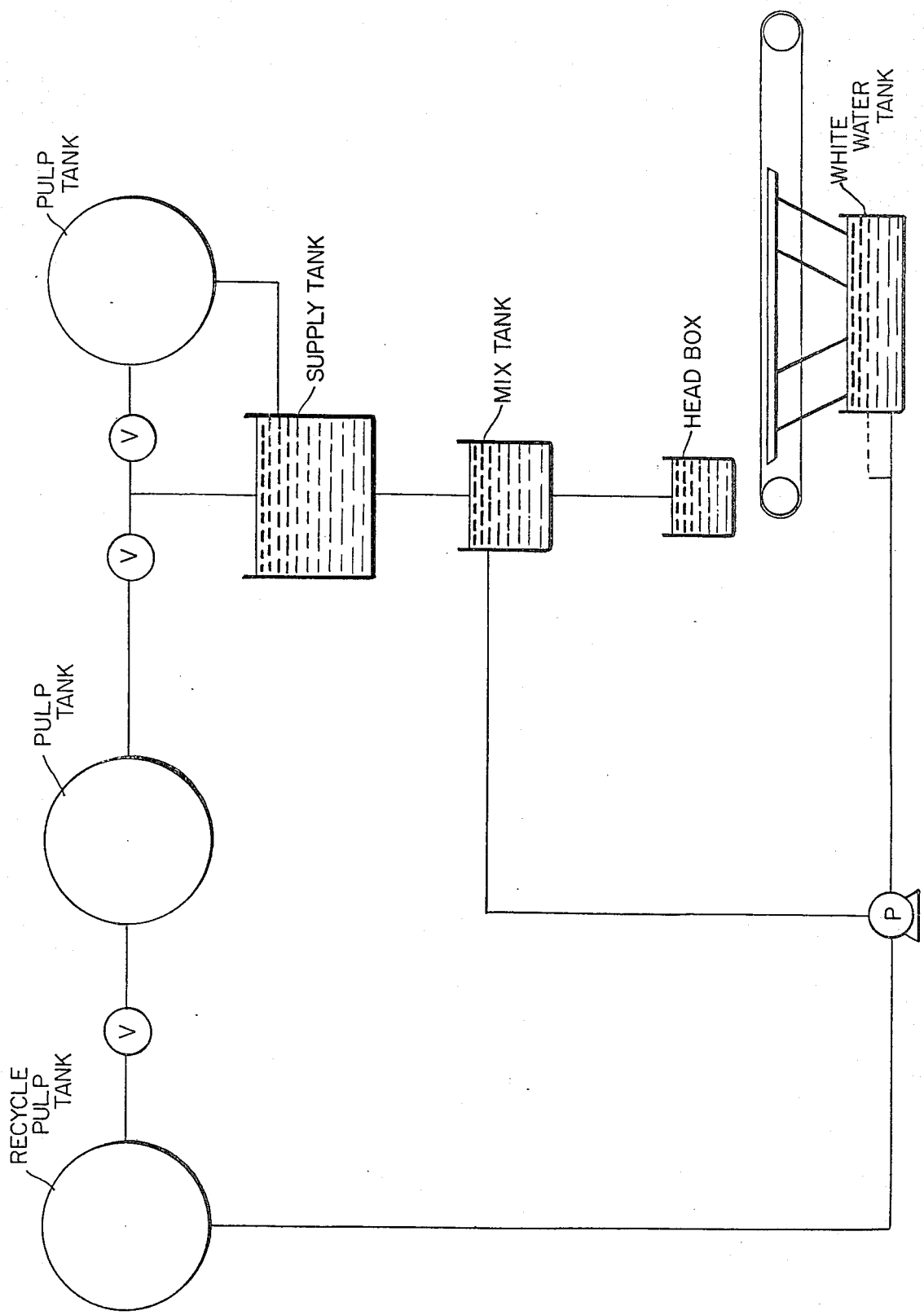

ENZYMATIC CATALYZED BIOCIDE SYSTEM

This is a continuation of application Ser. No. 319,298, filed Nov. 9, 1981 now U.S. Pat. No. 4,370,199.

BACKGROUND OF INVENTION

The present invention relates generally to a biocidal composition for use in industrial process streams and more particularly to an enzymatic catalyzed biocide system for pulp and paper mill process streams.

Microorganisms, particularly bacteria, are known to contaminate industrial process waters and may create slime deposits of biological origin. This is particularly true in the case of pulp and paper mill process streams where slime deposits formed by microorganisms are a common occurrence. Such deposits give rise to many problems including fouling or plugging of pipes and filters, and of greater significance, breakouts of spots and the like in the paper produced with consequent loss of production and work stoppages for clean up. These and other problems produced by slime deposits have resulted in the extensive utilization of biocides to prevent the growth of microorganisms in industrial waters.

Materials which have heretofore enjoyed widespread use in such applications include chlorine and a wide variety of proprietary chemical biocides. Other physical and chemical methods for slime control including gamma radiation, filtration and ozonation have been successfully used, but only in small scale applications, because such methods are costly and difficult to scale up to commercial size industrial processes. The use of chlorination to prevent the growth of microorganisms is also limited both by its cost effectiveness and the fact that chlorine is an active chemical that may react in solution before its full biocidal function is achieved. Meanwhile, other biocides suffer from odor problems and various hazards with respect to storage, use and handling, and the fact that most biocides are selective in their activity. As a consequence, the use of known biocidal systems involves careful selection and deployment, and the continuous or frequent addition to a plurality of points in the process stream.

SUMMARY OF INVENTION

It is an object of the present invention to provide a chemical biocide system capable of killing a wide spectrum of microorganisms for disinfecting industrial process waters.

It is a further object to provide a chemical biocide system that is particularly useful for controlling the growth of slime deposits in pulp and paper mill process waters.

Unlike the known proprietary biocides available, the biocide system of the present invention is characterized as an enzymatically catalyzed process that may utilize one or more components of the process stream to be treated. While the mechanism of the invention is not completely understood, it is based on the observation that peroxidase enzymes in the presence of hydrogen peroxide will oxidize phenolic compounds to quinones or hydroquinones that are toxic to microorganisms. This reaction produces an antibacterial activity that is a function of the type of quinone produced and the degree of phenolic polymerization. Since some industrial process streams are known to include phenolic compounds such as black liquor and other lignin derived phenolics, the present invention is capable of using one or more of the components of the process stream to be treated. Where the process stream is deficient in oxidizable phenolic compounds, these may be added as needed. The present invention also contemplates the use of other microbial or plant dehydrogenase enzymes such as laccase to generate the antibacterial activity.

The enzymatically catalyzed biocide system disclosed herein is not toxic to humans, it is water soluble, it contains no additives that may be deleterious to industrial process water, and has demonstrated a biocidal activity with respect to a wide variety of microorganisms. In addition, tests have shown that the enzymatic biocide system disclosed herein is economical, and comparable in efficiency to the known proprietary chemical biocides.

The use of peroxidase enzymes with various monophenolic compounds to generate antibacterial activity is known with respect to the generation of host defense mechanisms in plants and animals. However, applicant is the first to suggest and apply the same enzymatic reaction to an industrial process water disinfection biocide.

DETAILED DESCRIPTION

The enzymatically catalyzed biocide system of the present invention is effective even at low concentrations for controlling the growth of a wide variety of microorganisms. Such microorganisms may comprise bacteria selected from the group consisting of aerobic bacteria, e.g., Pseudomonas, Azotobacter, Staphylococcus and Bacillus; facultative anaerobic bacteria, e.g., Escherichia, Flavobacterium, Chromobacterium, Nitrobacter, Hyphomicrobrium and Sphaerotilus; and anaerobic bacteria, e.g., Desulfovibrio, Clostridium and Veillonella. In addition, the biocide system is useful in controlling the growth of and killing actinomycetes, fungi and yeasts. Moreover, the antibacterial activity and cost of the enzymatic biocide disclosed herein has been found to be comparable to that of proprietary chemical biocides presently on the market.

The preferred dehydrogenase enzyme for practicing the present invention is from the peroxidase family and more specifically is a plant peroxidase, e.g., from horseradish, turnip, etc. However in the event that hydrogen peroxide is not the oxidant of choice, the enzyme laccase could be substituted for horseradish peroxidase. Where laccase is used, the preferred oxidant is oxygen. Meanwhile, since the biocide system disclosed herein requires the presence of an oxidizable substrate, several sources are contemplated. For instance, a survey of useful phenolic substrates includes catechol, guaiacol, acid lignin, black liquor and resorcinol.

Peroxidase enzymes are fairly ubiquitous, occurring in higher plants, yeasts, molds, bacteria and mammals. They catalyze the dehydrogenation of a large number of organic compounds such as phenols and aromatic amines, hydroquinones and hydroquinoid amines, especially benzidine derivatives. Meanwhile, horseradish peroxidase is a protein material of about 40,000 MW (molecular weight) and is derived from a renewable raw material, namely the horseradish plant. The horseradish peroxidase enzyme has a long shelf life and is thermotolerant, i.e., its catalytic activity remains high over a wide temperature and pH range on the order of from about 10–60 degrees C., and pH 4–11 respectively.

Horseradish peroxidase and other peroxidases have been used to generate antibacterial activity in plants and animals with peroxidase-catalyzed dehydrogenation products. In fact, most peroxidases seem to be capable of wide spectrum antimicrobial activity, including activity towards yeasts, fungi and viruses. However, the present invention represents the first attempt to utilize such catalyzed dehydrogenation products for the disinfection of industrial process waters either under static or dynamic conditions.

The invention herein will be better understood with reference to the following examples. However, it is to be understood that the examples are intended to be illustrative only and not in any way limiting of the invention as a whole.

In the following examples, samples of papermachine white water (a general term for all waters of a paper mill which have been separated from the stock or pulp suspension), were aseptically taken from several papermachines and stored at 4 degrees C. until used. Horseradish peroxidase having an activity of 250 purpurogallin units/mg was purchased commercially from Sigma Chemical Company, St. Louis, Mo. The horseradish proxidase was prepared as 50 Units/ml stock solution and stored in the dark at 4 degrees C. until used. Activity of the diluted stock was measured daily during the tests.

EXAMPLE I

The enzymatically catalyzed biocide system consisted of 60 μl horseradish peroxidase (5 Units/ml) and 0.14 μl hydrogen peroxide and 1 mM guaiacol for enhancement where indicated. These reagents were added to a test tube, followed by the addition of 0.3 ml *E. coli* ATCC 25922 bacteria suspension and white water for a total volume of 3.0 ml. Horseradish peroxidase (HRP) enzyme activity was always greater than 95%. *E. coli* bacteria were added to increase the number of bacteria already present in the non-sterile white water to a measurable level in the assay. The assay reaction mixtures were incubated 30 minutes at 35 Degrees C. and the number of viable bacteria after incubation determined in triplicate by the spread plate technique on nutrient agar plates.

TABLE I

| Antibacterial Activity of HRP | | |
|---|---|---|
| White Water Samples | Treatment (% Kill) | |
| Papermachine (PM) | HRP | HRP + mM Guaiacol |
| #5 | 94.6 | 94.5 |
| #8 | 92.9 | 79.4 |
| #1 | 24.1 | 36.3 |
| #2 | 0 | 50 |
| #1 | 11.3 | 36.7 |

The data in Table 1 shows excellent antibacterial activity of the enzymatic catalyzed biocide system in #5 and #8 papermachines (PM). These samples were taken from a papermachine used for manufacturing bleached board. However, the antibacterial activity of samples taken from PM's #1 and #2 making kraft paper were unacceptably low. The addition of 1 mM Guaiacol as an oxidizable substrate resulted in an increase in the antibacterial activity only in #1 and #2 PM's. The inhibition of bacterial activity in the latter papermachine systems was found to be due to the presence of material of particle size greater than 1.2 μm which inactivated the enzyme. The data also shows that significant differences in the antibacterial activity of the biocide system may occur from time to time due to the presence of enzyme poisons such as sulfide or other reducing agents which sequester the oxidation products of the enzyme reaction. In the examples where no guaiacol was added, the phenolic substrate relied on for antibacterial activity of the biocide system was the black liquor contamination, from the pulping process, normally found in papermachine process water.

EXAMPLE II

In another experiment using the test procedure described above for Example I, enhancement of the antibacterial activity of the HRP biocide system was measured using different quantities of guaiacol. The results are shown in Table II.

TABLE II

| Antibacterial Activity of HRP + Guaiacol | | | | |
|---|---|---|---|---|
| Treatment Guaiacol (mM) | White Water Samples (PM) (% Kill) | | | |
| | #5 | #8 | #1 | #2 |
| 0 | — | 52.5 | 0 | 11.3 |
| 0.0001 | 0 | 86.8 | — | — |
| 0.01 | 0 | 91.0 | 57.2 | 39.8 |
| 0.1 | 19.9 | 97.6 | 49.3 | 36.5 |
| 1 | 80.7 | 100 | 2.8 | 4.3 |
| 10 | 97.4 | 100 | 38.6 | 46.1 |

As shown in Table II, the addition of guaiacol appears to enhance the antibacterial activity of the biocide system at least for the bleached board water samples. The presence of a sequestering agent in the raw water limited the amount of antibacterial activity in these samples to no more than about 50% kill. In each of the samples, the black liquor concentration was assumed to be constant and as before the normal microflora of these samples were enriched with the addition of 0.3 ml *E. coli* ATCC 26922 bacteria suspension.

EXAMPLE III

In another test, the effect of several monophenolic compounds on the short term (30 minutes) killing of bacteria, and long term (3 hours) inhibition of bacterial growth by the HRP biocide system was determined. The white water samples used were taken from kraft papermachine process waters containing a mixed population of bacteria such as Pseudomonae, Bacillus, Desulfovibrio and Flavobacterium. In this assay, a 1.0 ml white water sample was added to 50 ml of nutrient broth and incubated overnight at 37 degrees C. with shaking. The resulting bacteria were harvested by centrifugation at 7000 rpm and resuspended in an equal volume of white water. These bacteria were then added to white water samples in order to fortify the total number of active indigenous bacteria. The assays were completed as set forth in Example I. The results are set forth in Table III.

TABLE III

| Antibacterial Activity of HRP System With Several Phenolic Compounds Kraft Papermachine Process Water | | | |
|---|---|---|---|
| Phenolic Compound | Phenolic Concentration | % Kill | |
| | | 0.5 hour | 3.0 hours |
| Catechol | $10^{-2}$M | 99.85 | 99.97 |
| | $10^{-3}$M | 99.85 | 99.94 |
| Guaiacol | $10^{-2}$M | 99.85 | 99.97 |
| | $10^{-3}$M | 29.2 | 36.88 |
| Neutral Black Liquor | 5 μg/ml | 38.36 | 40.43 |
| | 10 μg/ml | 43.85 | 41.61 |

The data in Table VI suggest that the peroxidase system amended with various monophenolic compounds is effective against a mixed population of bacteria indigenous to a mill process water stream with no apparent regrowth of bacteria after extended periods of incubation. The practical implications of these findings are that the peroxidase-monophenolic system can be used for long term killing and inhibition of diverse population of bacteria in a paper mill process water stream.

It will, therefore, be appreciated that the present invention provides an effective control for regulating the growth of a wide variety of bacteria, fungi and yeasts in process water systems. The invention utilizes an enzymatically catalyzed system which employs a microbial or plant dehydrogenase enzyme such as peroxidase or laccase. Thus, whereas only particular embodiments of the invention have been described herein for purposes of illustration, it will be evident to those skilled in the art that numerous variations in the details disclosed may be made without departing from the invention as defined in the appended claims.

I claim:

1. A method for enzymatically killing and controlling the growth of microorganisms in an industrial process wastewater stream comprising:
   (a) adding to the stream an effective amount of a plant or microbial dehydrogenase enzyme selected from the group consisting of peroxidase and laccase;
   (b) adding to the stream an oxidant selected from the group consisting of oxygen and hydrogen peroxide;
   (c) adding to the stream a sufficient quantity of an oxidizable monophenolic compound selected from the group consisting of black liquor, catechol, guaiacol, resorcinol and lignin to achieve the desired kill and control; and,
   (d) reacting the dehydrogenase enzyme and oxidant in the stream to produce a catalytic oxidation of the monophenolic compound thereby producing quinone and hydroquinone derivatives that are toxic to the microorganisms in the stream.

2. A method for enzymatically killing and controlling the growth of microorganisms in an industrial process wastewater stream by the catalytic oxidation of monophenolic compounds added to or naturally occurring in the stream comprising:
   (a) adding to the stream an effective amount of a plant or microbial dehydrogenase enzyme selected from the group consisting of peroxidase and laccase;
   (b) adding to the stream an oxidant selected from the group consisting of oxygen and hydrogen peroxide;
   (c) adding to the stream a sufficient quantity of an ozidizable monophenolic compound selected from the group consisting of black liquor, catechol, guaiacol, resorcinol and lignin to achieve the desired kill and control; and,
   (d) reacting the ingredients to produce quinone and hydroquinone reaction products in situ within the wastewater stream which are toxic to the microorganisms in the stream.

3. The method of claim 2 wherein the quantity of enzyme and oxidant added to the wastewater stream is sufficient to oxidize all of the monophenolic oxidizable compound material naturally occurring or added to the stream.

4. The method of claim 3 wherein the wastewater stream may have a pH of from about 4–11 and a temperature of from about 10–60 degrees C.

5. The method of claim 4 wherein the dehydrogenase enzyme is peroxidase and the oxidant is hydrogen peroxide.

6. The method of claim 4 wherein the dehydrogenase enzyme is laccase and the oxidant is oxygen.

* * * * *